US012611272B2

(12) United States Patent
Vadali et al.

(10) Patent No.: US 12,611,272 B2
(45) Date of Patent: Apr. 28, 2026

(54) SURGICAL ROBOTIC SYSTEM WITH USER ENGAGEMENT MONITORING

(71) Applicant: Covidien LP, Mansfield, MA (US)

(72) Inventors: K V S Manoj Kumar Vadali, Hyderabad (IN); Sweta Anil Nawate, Bengaluru (IN)

(73) Assignee: Covidien LP, Mansfield, MA (US)

( * ) Notice: Subject to any disclaimer, the term of this patent is extended or adjusted under 35 U.S.C. 154(b) by 6 days.

(21) Appl. No.: 18/294,242

(22) PCT Filed: Sep. 7, 2022

(86) PCT No.: PCT/US2022/042681
§ 371 (c)(1),
(2) Date: Feb. 1, 2024

(87) PCT Pub. No.: WO2023/038918
PCT Pub. Date: Mar. 16, 2023

(65) Prior Publication Data
US 2024/0350213 A1 Oct. 24, 2024

Related U.S. Application Data

(60) Provisional application No. 63/242,122, filed on Sep. 9, 2021.

(51) Int. Cl.
*A61B 34/37* (2016.01)
*A61B 17/00* (2006.01)
(Continued)

(52) U.S. Cl.
CPC .............. *A61B 34/37* (2016.02); *A61B 90/37* (2016.02); *A61B 2017/00199* (2013.01); *A61B 2017/0046* (2013.01); *A61B 2034/2057* (2016.02)

(58) Field of Classification Search
CPC ......... A61B 34/20; A61B 34/30; A61B 34/37; A61B 34/77; A61B 2034/2057;
(Continued)

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |

(Continued)

FOREIGN PATENT DOCUMENTS

| | | |
|---|---|---|
| WO | 2019152771 A1 | 8/2019 |
| WO | 2020243192 A1 | 12/2020 |
| WO | 2021118750 A1 | 6/2021 |

OTHER PUBLICATIONS

International Search Report and Written Opinion of the International Searching Authority issued in corresponding application PCT/US2022/042681 mailed Dec. 13, 2022 (12 pages).
(Continued)

*Primary Examiner* — Tuan V Nguyen
(74) *Attorney, Agent, or Firm* — Carter, DeLuca & Farrel

(57) ABSTRACT

A robotic surgical system includes a surgical console with a tracking device for determining whether a user is engaged with the surgical console and controls a mode of operation of at least one component of the robotic surgical system based on whether or not the user is engaged with the surgical console.

17 Claims, 7 Drawing Sheets

(51) Int. Cl.
   *A61B 34/20* (2016.01)
   *A61B 90/00* (2016.01)

(58) Field of Classification Search
   CPC .. A61B 2017/0046; A61B 2017/00199; A61B 90/06
   See application file for complete search history.

(56) References Cited

U.S. PATENT DOCUMENTS

| | | | |
|---|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |

(56) References Cited

U.S. PATENT DOCUMENTS

| | | | |
|---|---|---|---|
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,852,174 | B2 | 10/2014 | Burbank |
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |

(56) References Cited

U.S. PATENT DOCUMENTS

| | | |
|---|---|---|
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,376,002 B2 | 7/2022 | Shelton, IV et al. |
| 11,376,098 B2 | 7/2022 | Shelton, IV et al. |
| 11,381,759 B2 | 7/2022 | Zhao et al. |
| 11,382,621 B2 | 7/2022 | Scheib et al. |
| 11,382,624 B2 | 7/2022 | Harris et al. |
| 11,382,625 B2 | 7/2022 | Huitema et al. |
| 11,382,626 B2 | 7/2022 | Shelton, IV et al. |
| 11,382,627 B2 | 7/2022 | Huitema et al. |
| 11,382,638 B2 | 7/2022 | Harris et al. |
| 11,382,644 B2 | 7/2022 | Schoettgen et al. |
| 11,389,160 B2 | 7/2022 | Shelton, IV et al. |
| 11,389,255 B2 | 7/2022 | DiMaio et al. |
| 11,399,906 B2 | 8/2022 | Shelton, IV et al. |
| 11,406,379 B2 | 8/2022 | Hess et al. |
| 11,410,259 B2 | 8/2022 | Harris et al. |
| 11,419,630 B2 | 8/2022 | Yates et al. |
| 11,424,027 B2 | 8/2022 | Shelton, IV |
| 11,432,888 B2 | 9/2022 | Diolaiti et al. |
| 11,432,893 B2 | 9/2022 | Itkowitz et al. |
| 11,432,895 B2 | 9/2022 | Loh et al. |
| 11,439,390 B2 | 9/2022 | Patel et al. |
| 11,439,391 B2 | 9/2022 | Bruns et al. |
| 11,468,791 B2 | 10/2022 | Jarc et al. |
| 11,471,155 B2 | 10/2022 | Shelton, IV et al. |
| 11,471,221 B2 | 10/2022 | Zhao et al. |
| 11,478,308 B2 | 10/2022 | Hoffman et al. |
| 11,490,977 B2 | 11/2022 | Schena et al. |
| 11,497,499 B2 | 11/2022 | Shelton, IV et al. |
| 11,504,119 B2 | 11/2022 | Shelton, IV et al. |
| 11,504,124 B2 | 11/2022 | Patel et al. |
| 11,510,743 B2 | 11/2022 | Shelton, IV et al. |
| 11,517,312 B2 | 12/2022 | Wixey |
| 11,517,325 B2 | 12/2022 | Shelton, IV et al. |
| 11,518,048 B2 | 12/2022 | Saraliev et al. |
| 2009/0326556 A1* | 12/2009 | Diolaiti ............. A61B 1/00149<br>606/130 |
| 2020/0015918 A1* | 1/2020 | Payyavula ............ B25J 9/1689 |
| 2020/0107727 A1* | 4/2020 | Piponi .............. G06F 18/24155 |
| 2020/0397529 A1 | 12/2020 | Anderson et al. |

OTHER PUBLICATIONS

Communication Pursuant to Article 94(3) EPC issued in European Application No. 22 783 113.8 dated Nov. 20, 2025, 10 pages.

* cited by examiner

320

321a        162        321b

163

164a

164d 164b     164c     164e

SURGICAL ROBOTIC SYSTEM WITH USER ENGAGEMENT MONITORING

CROSS REFERENCE TO RELATED APPLICATIONS

This application is a U.S. National Stage Application filed under 35 U.S.C. § 371 (a) of International Patent Application No. PCT/US2022/042681, filed on Sep. 7, 2022, which claims the benefit of the filing date of provisional U.S. Patent Application No. 63/242,122, filed on Sep. 9, 2021. The entire disclosures of the foregoing applications are incorporated by reference herein.

FIELD

The present disclosure generally relates to a surgical robotic system including one or more components that are switchable between a normal mode of operation and an efficiency mode of operation based on user engagement.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm.

For any electro-mechanical system, the reliability and life expectancy of the system depends on a variety of factors, such as the temperature at which it is operated. Power consumption of surgical robotic systems causes heat generation which, in the long-term, reduces the life expectancy of the system, and in the short-term, increases the risk of system-failure during operation. Additionally, the excessive usage of bandwidth during operation of a remotely operated surgical robotic system poses a boundary to tele-surgical implementations.

SUMMARY

The present disclosure provides for a surgical robotic system including one or more components that are switchable between a normal mode of operation and an efficiency mode of operation based on user engagement to reduce bandwidth occupancy, power consumption, and heat generation during operation.

In one aspect of the present disclosure, a robotic surgical system is disclosed and includes a robotic arm and a surgical console. The robotic arm includes a camera having a light emitter and being configured to transmit video. The surgical console includes a handle communicatively coupled to at least one of the robotic arm or the camera, a display device configured to display video transmitted from the camera, a tracking device, and a computer. The tracking device includes image capture device configured to capture an image of a user position reference point. The computer is configured to compute, based on the captured image, a position of the user position reference point relative to the display device and determine whether a user is engaged with or disengaged from the surgical console based on the computed position. In response to a determination that the user is disengaged from the surgical console for a predetermined amount of time, the computing device is configured to perform at least one of the following: cause the camera to reduce video transmission quality or cause the camera to stop video transmission; reduce a brightness level of the display device or reduce an intensity of the light emitter of the camera; or adjust internal communication parameters between components of the robotic surgical system.

In an aspect, in response to a determination that the user is disengaged from the surgical console for a predetermined amount of time, the computer is configured to cause the camera to reduce video transmission quality by reducing a baud rate of the camera.

In an aspect, in response to a determination that the user is disengaged from the surgical console for a predetermined amount of time, the computer is configured to cause the camera to stop video transmission and reduce the brightness level of the display device.

In an aspect, in response to a determination that the user is disengaged from the surgical console for a predetermined amount of time, the computer is configured to cause the camera to reduce video transmission quality, or stop video transmission, and reduce the intensity of the light emitter.

In an aspect, the robotic surgical system includes a control tower including a second display device configured to display video transmitted by the camera.

In an aspect, in response to a determination that the user is disengaged from the surgical console for a predetermined amount of time, the computer is configured to cause the camera to reduce video transmission quality to the second display device of the control tower and cause the camera to maintain video transmission quality to the display device of the surgical console.

In an aspect, in response to a determination that the user is disengaged from the surgical console for a predetermined amount of time, the computer is configured to cause the camera to reduce video transmission quality to the display device of the surgical console and cause the camera to reduce video transmission quality to the second display device of the control tower.

In an aspect, in response to a determination that the user is disengaged from the surgical console for a predetermined amount of time, the computer is configured to cause the camera to stop video transmission to the display device of the surgical console and cause the camera to stop video transmission to the second display device of the control tower.

In another aspect of the present disclosure, a robotic surgical system is disclosed and includes a camera and a surgical console. The camera is configured to transmit video to the surgical console. The surgical console includes a handle communicatively coupled to a surgical instrument, a display device configured to display video transmitted from the camera, a tracking device configured to track a position of a user operating the surgical console, and a computer. The computer is configured to determine whether a user is engaged with or disengaged from the display device of the surgical console based on the tracked position of the user operating the surgical console. In response to a determination that the user is disengaged from the surgical console for a predetermined amount of time, the computer is configured to perform at least one of the following: cause the camera to reduce video transmission quality or cause the camera to stop video transmission; reduce a brightness level of the display device; or adjust internal communication parameters between components of the robotic surgical system.

In an aspect, in response to a determination that the user is disengaged from the surgical console for a predetermined amount of time, the computer is configured to cause the camera to reduce video transmission quality by reducing a baud rate of the camera.

In an aspect, in response to a determination that the user is disengaged from the surgical console for a predetermined amount of time, the computer is configured to cause the camera to stop video transmission and reduce the brightness level of the display device.

In an aspect, the camera includes a light emitter and, in response to a determination that the user is disengaged from the surgical console for a predetermined amount of time, the computer is configured to cause the camera to reduce video transmission quality, or stop video transmission, and reduce an intensity of the light emitter.

In an aspect, the robotic surgical system includes a control tower including a second display device configured to display video transmitted by the camera.

In an aspect, in response to a determination that the user is disengaged from the surgical console for a predetermined amount of time, the computer is configured to cause the camera to reduce video transmission quality to the second display device of the control tower and cause the camera to maintain video transmission quality to the display device of the surgical console.

In an aspect, in response to a determination that the user is disengaged from the surgical console for a predetermined amount of time, the computer is configured to cause the camera to reduce video transmission quality to the display device of the surgical console and cause the camera to reduce video transmission quality to the second display device of the control tower.

In an aspect, in response to a determination that the user is disengaged from the surgical console for a predetermined amount of time, the computer is configured to cause the camera to stop video transmission to the display device of the surgical console and cause the camera to stop video transmission to the second display device of the control tower.

In another aspect of the present disclosure, a robotic surgical system is provided and includes a robotic arm, a control tower, and a surgical console. The robotic arm includes a camera having a light emitter and being configured to transmit video. The control tower includes a first display device configured to display video transmitted from the camera. The surgical console includes a handle communicatively coupled to at least one of the robotic arm or the camera, a second display device configured to display video transmitted from the camera, a tracking device including an image capture device configured to capture an image of a user position reference point, and a computer. The computer is configured to determine whether a user is engaged with or disengaged from the second display device of the surgical console based on the tracked position of the user operating the surgical console. In response to a determination that the user is disengaged from the surgical console for a predetermined amount of time, the computer is configured to perform at least one of the following: cause the camera to reduce video transmission quality or cause the camera to stop video transmission; reduce a brightness level of the first display device or the second display device or reduce an intensity of the light emitter of the camera; or adjust internal communication parameters between components of the robotic surgical system.

In an aspect, in response to a determination that the user is disengaged from the surgical console for a predetermined amount of time, the computer is configured to cause the camera to reduce video transmission quality by reducing a baud rate of the camera.

In an aspect, in response to a determination that the user is disengaged from the surgical console for a predetermined amount of time, the computer is configured to cause the camera to stop video transmission, reduce the brightness level of the second display device, and maintain the brightness level of the first display device.

In an aspect, in response to a determination that the user is disengaged from the surgical console for a predetermined amount of time, the computer is configured to cause the camera to reduce video transmission quality or stop video transmission and reduce the intensity of the light emitter.

BRIEF DESCRIPTION OF THE DRAWINGS

Various embodiments of the present disclosure are described herein with reference to the drawings wherein.

DETAILED DESCRIPTION

Figure 1:
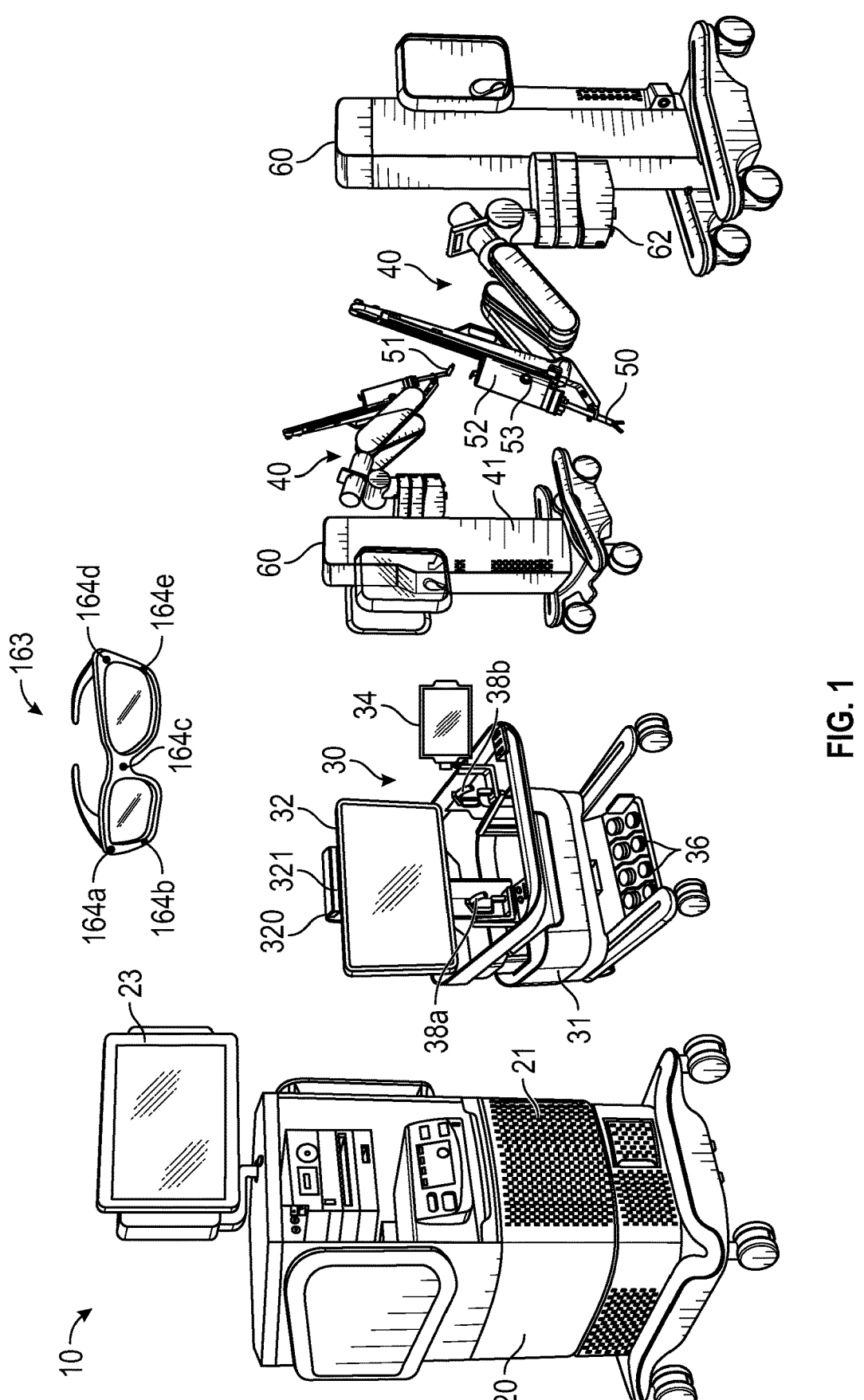
FIG. 1 is a schematic illustration of a surgical robotic system including a control tower, a console, and one or more surgical robotic arms according to an embodiment of the present disclosure.

The present disclosure is directed to robotic surgical systems, devices, methods, and computer-readable media that reduce energy consumption, heat generation, and/or bandwidth expenditure of one or more components of the robotic surgical system when such resources are needed least. More particularly, the present disclosure relates to systems and methods for identifying disengagement of a user using the robotic surgical system and causing the robotic surgical system to operate in one or more efficiency modes when the user is disengaged, thereby extending the life of the components of the robotic surgical system, reducing heat generation within the surgical setting, and enhancing the performance and communication between the components of the robotic surgical system. The systems and methods described herein provide various techniques for tracking a user position relative to a display of a surgical console and, based on the tracked user position, determining whether the user is disengaged from a surgical console, even for open-console architectures. If the user is disengaged from the surgical console, the robotic surgical system is operated in one or more efficiency modes. Utilizing the technologies, techniques, and embodiments described herein, users are provided with a safer operating environment in which to perform robotic surgeries, patients are afforded a safer environment in which to receive surgical treatment via robotic surgical systems, communication speed and reliability between the components of the robotic surgical system is increased, and the life expectancy of the components of the robotic surgical system is extended.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a computer, a controller, or on a user device, including, for example, a mobile device, an IoT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60. The surgical robotic system 10 is configured to determine whether or not a user is engaged with the surgical console 30 of the surgical robotic system 10 and, based on that determination, cause one or more of the components of the surgical robotic system 10 to operate in one of various operational modes, including one or more efficiency modes or normal modes. As described below, the types of efficiency modes in which the components of the surgical robotic system 10 are configured to operate include, but are not limited to (1) an efficiency mode based on reducing the quality of the video transmission to the surgical console 30 and the control tower 20, (2) an efficiency mode based on stopping the video transmission to the surgical console 30 and the control tower 20, (3) an efficiency mode based on reducing the quality of the video transmission to the surgical console 30, while maintaining the quality of the video transmission to the control tower 20, (4) an efficiency mode based on reducing the brightness, turning off, or switching to standby, at least one of the display devices (e.g., first display 32, second display 23, etc.), and/or (5) an efficiency mode based on reducing the intensity of a light emitter of the camera 51 or of another light emitter within the surgical setting. Additional details of determining whether a user is engaged with, or disengaged from, the surgical robotic system 10 and, in response, causing one or more components of the surgical robotic system 10 to operate in normal modes or efficiency modes are provided herein in the context of FIGS. 7A-7C and 8.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscope camera 51, configured to provide a video feed for the clinician which is transmitted to any of the control tower 20, the surgical console 30, or the robotic arm 40. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

One of the robotic arms 40 may include a camera 51 configured to capture video of the surgical site. The surgical console 30 includes a first display 32, which displays a video feed of the surgical site transmitted by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38a and 38b which are used by a user to remotely control robotic arms 40. The surgical console 30 further includes an armrest 33 used to support clinician's arms while operating the handle controllers 38a and 38b.

The control tower 20 includes a display 23, which may be a touchscreen, and outputs on the graphical user interfaces (GUIs) which may include a display of the video feed transmitted by the camera 51. The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
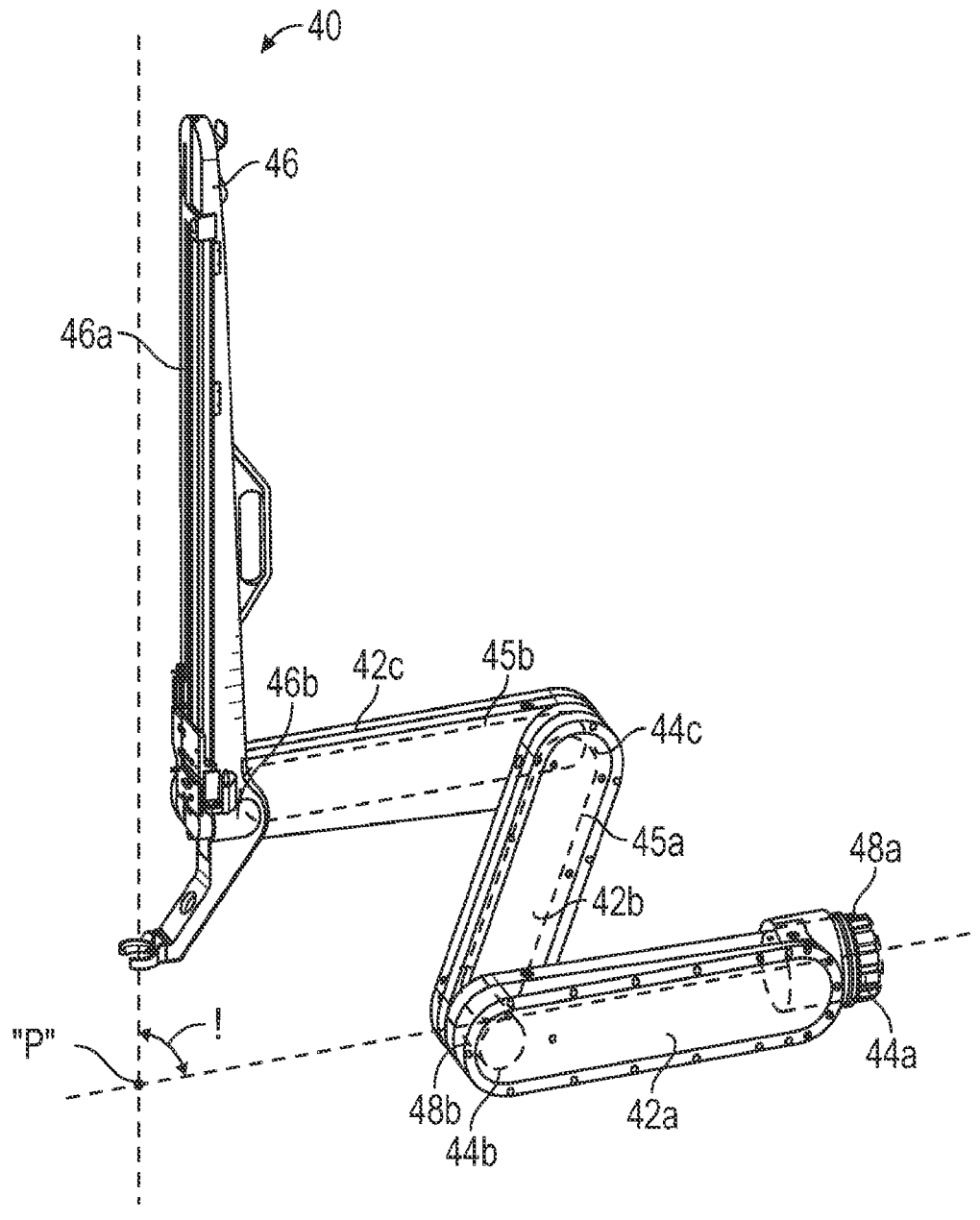
FIG. 2 is a perspective view of a surgical robotic arm of the surgical robotic system of FIG. 1 according to an embodiment of the present disclosure.
Figure 3:
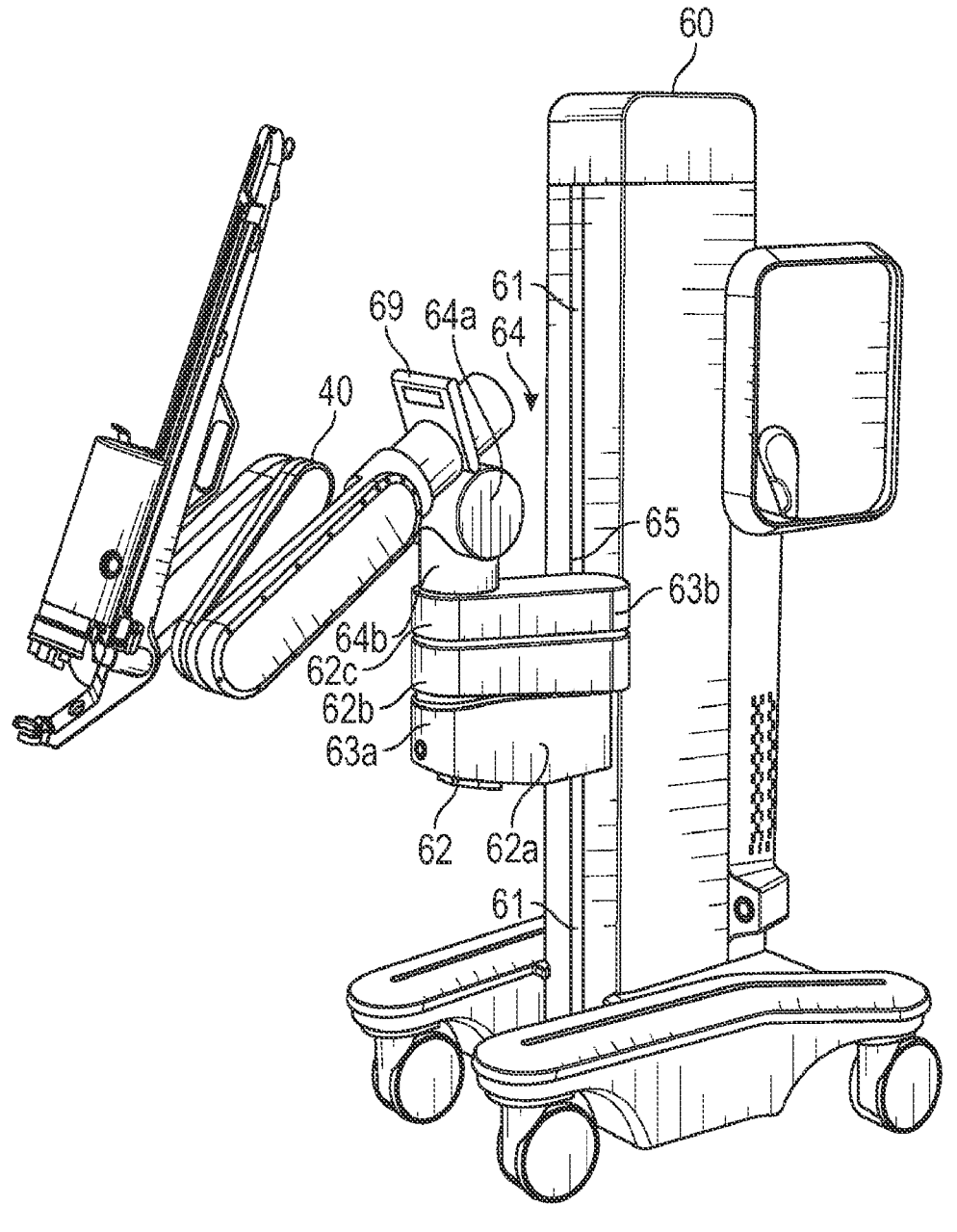
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effectors) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c.

The robotic arm 40 also includes a plurality of manual override buttons 53 disposed on the IDU 52 and the setup arm 62, which may be used in a manual mode. The clinician may press one or the buttons 53 to move the component associated with the button 53.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a remote center point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
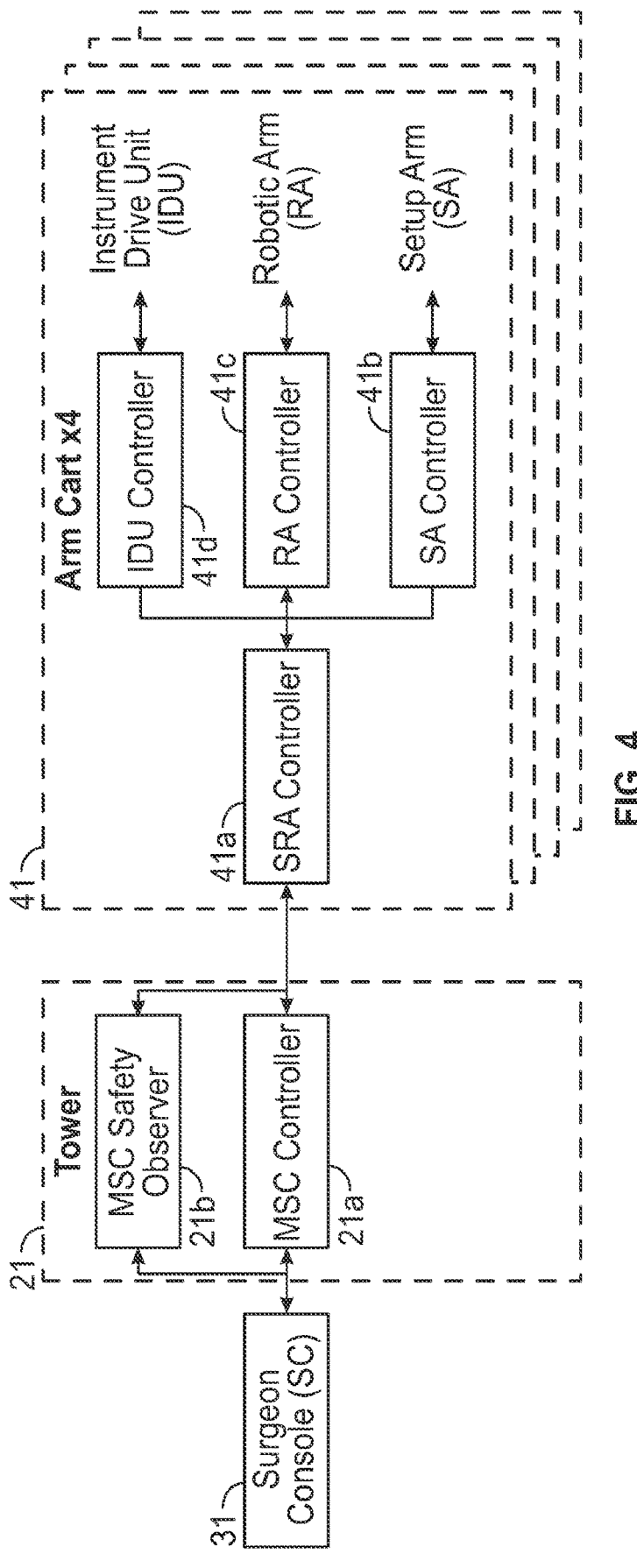
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The handle controllers 38a and 38b include one or more haptic feedback vibratory devices that output a haptic feedback. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled as follows. Initially, a pose of the handle controller controlling the robotic arm 40, e.g., the handle controller 38*a*, is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38*a* is then scaled by a scaling function executed by the controller 21*a*. In embodiments, the coordinate position is scaled down and the orientation is scaled up by the scaling function. In addition, the controller 21*a* also executes a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
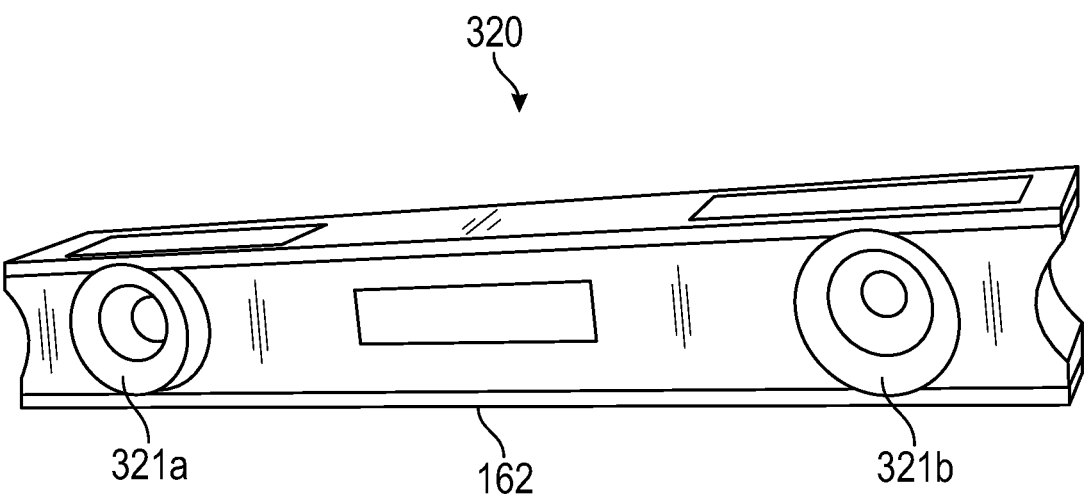
FIG. 5 is a perspective view of an optical tracking device according to an embodiment of the present disclosure.

With reference to FIGS. 1 and 5, the surgical console 30 includes an image tracking device 320, which includes one or more image capture devices 321 (referred to individually as image capture device 321*a* and image capture device 321*b*). By way of the tracking device 320, the surgical console 30 is configured to, in real-time or near real-time, identify and track a user position reference point (for example, a portion of a user or of wearables 163 worn by the user); determine whether the user is engaged with, or disengaged from, the surgical console 30; and cause one or more components of the surgical robotic system 10 to operate in a normal mode or an efficiency mode based on a result of the determination. As used herein, the term "user position reference point" generally refers to at least a portion of the user and/or at least a portion of an object (such as eyeglasses) that the surgical console 30 can utilize as a basis upon which to compute and/or track a position and/or an orientation of the user relative to a reference coordinate system, such as a coordinate system defined by a front plane of the first display 32 facing the user. In various embodiments, the user position reference point may include a single portion of the user or the object or include multiple portions of the user or the object. As used herein in this context, the term "a portion of a user" refers to any anatomical part of a user, including but not limited to, an eye, a pupil within an eye, a head, a face, and/or the like. Exemplary types of the one or more image capture devices 321 are image capture devices 321*a* and 321*b*, illustrated in FIG. 5. As shown in FIG. 5, the image capture devices 321*a* and 321*b* are positioned apart from each other. The surgical console 30 is configured to cause the image capture devices 321 to move to track the user portion reference point over one or more time periods. In some embodiments, the one or more image capture devices 321 are housed within a housing unit, such as housing unit 162, and the housing unit 162 is included within or attached to the surgical console 30.

Figure 6:
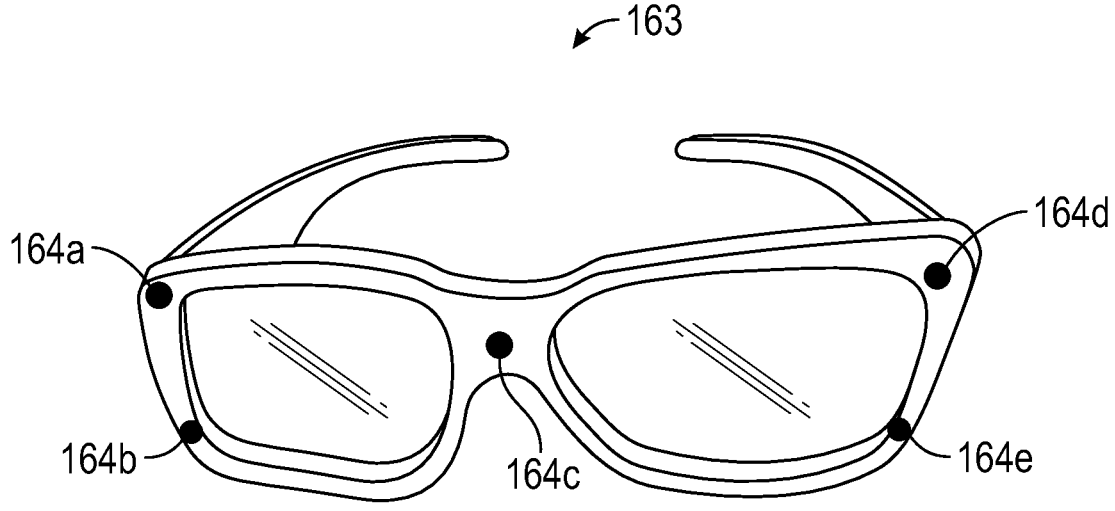
FIG. 6 is a perspective view of user wearables for tracking a user according to an embodiment of the present disclosure.

In some embodiments, the surgical console 30 is trained on one or more facial and/or feature recognition algorithms and is configured to detect eyes, pupils, a head, a face, and/or the like of a user by applying the one or more facial and/or feature recognition algorithms on one or more images captured by the image capture devices 321. In some embodiments, the surgical console 30 is configured to perform optical tracking of the user position reference point, and the one or more image capture devices 321 are equipped with infrared (IR) pass filters (not shown) in front of their lenses and a ring of IR light emitting diodes (LEDs) (not shown) around the lens. In optically tracking the user position reference point, the surgical console 30 periodically illuminates a desired space with IR light using the IR LEDs, and identifies and tracks the user position reference point by detecting the IR light reflections from markers placed on a portion of the user or on an object, such as the wearable 163, worn by the user, using the one or more image capture devices 321. An exemplary type of the wearable 163 including markers 164*a*, 164*b*, 164*c*, 164*d*, 164*e*, (collectively, 164), which may be reflective markers, positioned thereon is illustrated in FIG. 6.

Figure 7A:
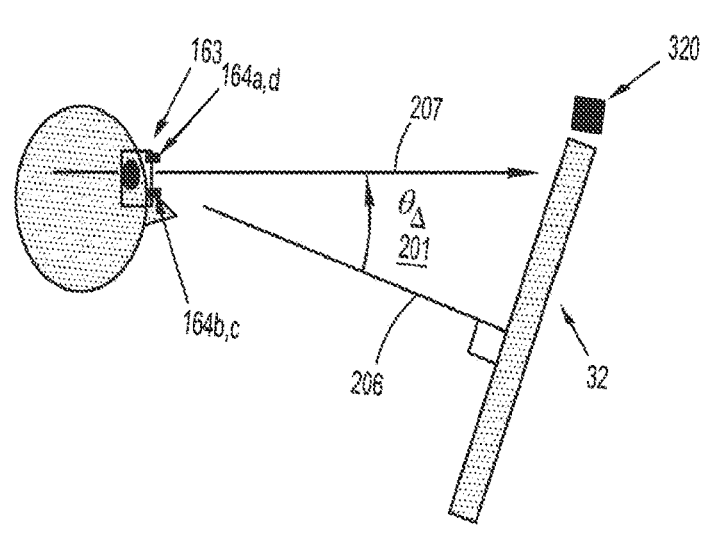
FIGS. 7A-7C illustrate exemplary aspects of how the surgical robotic system of FIG. 1 may be used to monitor user engagement.

Turning now to FIG. 7A, an exemplary arrangement of the first display 32 and the one or more image capture devices 321 is shown in accordance with one or more embodiments herein. The one or more image capture devices 321 are positionally affixed to the first display 32 such that the positional relationship between the image capture devices 321 and the first display 32 is known, and the surgical console 30 and/or the tracking device 320 are configured to determine whether a user is engaged with, or disengaged from, the surgical console 30 based in part on the positional relationship between the image capture devices 321 and the first display 32. In some embodiments, the positional relationship between the image capture devices 321 and the first display 32 is provided as an input to the surgical console 30, for example, by a user. The surgical console 30 may be configured to compute the positional relationship between the one or more image capture devices 321 and the first display 32, based on the orientation of the first display 32 relative to a fixed location of the environment in which the surgical console 30 is placed, such as the ground or floor of a room.

In tracking the user position reference point in real-time and over one or more time periods, the surgical console 30 computes a location of the user position reference point relative to the first display 32 in each of the time periods. The location of the user position reference point relative to the first display 32 is computed based in part on data related to the positional relationship between the one or more image capture devices 321 and the first display 32. In computing the location of the user position reference point relative to the first display 32, the surgical console 30 computes a position and an orientation of the user position reference point. The position of the user position reference point is computed in a three-dimensional coordinate space, for example, in an x, y, and z coordinate space, and the orientation of the user position reference point is computed by computing the roll, pitch, and yaw angles of the user position reference point. The position and the orientation of the user position reference point are computed relative to the first display 32.

Figure 7B:
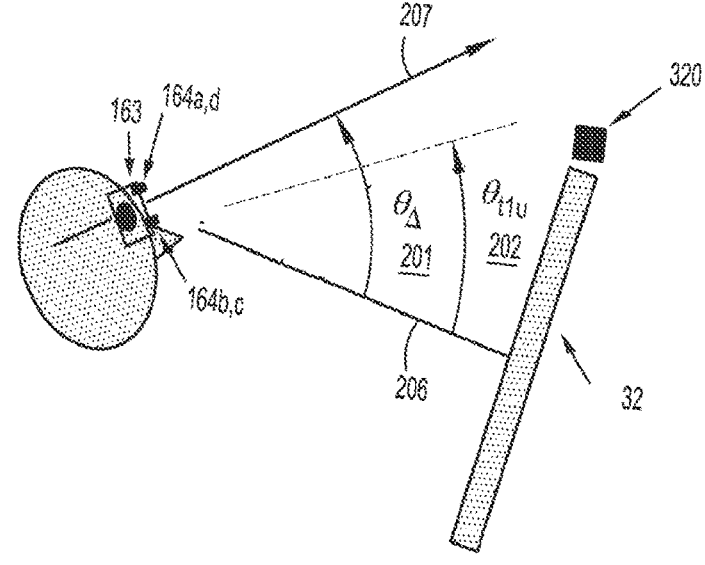
Figure 7C:
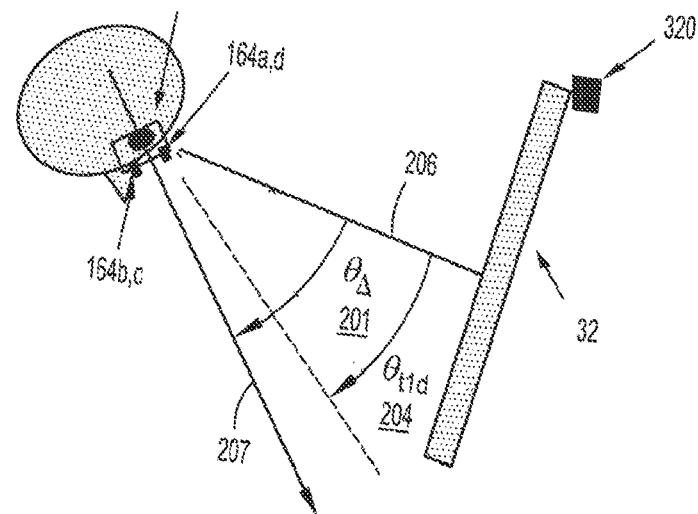

Using the position and the orientation of the user position reference point, the surgical console 30 computes a difference angle $\theta_A$. As used herein, the term "difference angle" is an angle between an imaginary line 206 normal or perpendicular to a front plane of the first display 32 and an imaginary line 207 normal to a plane formed by user position reference point(s) (for example, three user position reference points corresponding to three of the markers 164) being tracked. An example of such a difference angle $\theta_A$ is shown as difference angle $\theta_A$ 201 in FIG. 7A. The normal imaginary line 207 is substantially aligned with a direction in which the surgeon is looking. In the embodiment of FIGS. 7A-C, a user is wearing the wearable 163, which has the markers 164 positioned thereon, at least three markers 164 of which represents the user position reference points, and the surgical console 30 is performing optical tracking of the user position reference points. The surgical console 30 computes the difference angle $\theta_A$ 201 by computing a relative angle between the imaginary line 207 normal to the plane formed by the markers 164 and the imaginary line 206 normal to the front plane of the first display 32.

As the user's head moves, the position of the imaginary line 207 normal to the plane formed by the markers 164 changes from a first position (for example, the position shown in FIG. 7A) to a second position (for example, the positions shown in FIG. 7B or FIG. 7C), and accordingly the difference angle $\theta_A$ 201 changes, as shown in FIG. 7B and FIG. 7C. In embodiments where the surgical console 30 is tracking the user position reference points by detecting features of the user, such as the eyes of the user, the surgical console 30 computes the difference angle $\theta_A$ 201 by computing a position of an imaginary line (not shown in FIGS. 7A-7C) normal to the detected features of the user and a position of the imaginary line 206 normal to the front plane of the first display 32, and by computing an angle between the computed positions of the two imaginary lines. As the detected features move relative to the first display 32, the position of the imaginary line normal to the detected features changes and the difference angle $\theta_A$ 201 changes accordingly.

The surgical console 30 is configured to determine whether the user is engaged with, or disengaged from, the surgical console 30 or any components of robotic surgical system 10 based in part on the difference angle $\theta_A$ 201, that is when the difference angle $\theta_A$ 201 exceeds one or more thresholds. In particular, the surgical console 30 compares the difference angle $\theta_A$ 201, which was computed based on the position and the orientation of the user position reference point, to the first threshold angle $\theta_{t1u}$ 202 (FIG. 7B) and the second threshold angle $\theta_{t1d}$ 204 (FIG. 7C) and determines whether the difference angle $\theta_A$ 201 is greater than the first threshold angle $\theta_{t1u}$ 202 or the second threshold angle $\theta_{t1d}$ 204. If the surgical console 30 determines that the difference angle $\theta_A$ 201 is greater than the first threshold angle $\theta_{t1u}$ ("$\theta_A > \theta_{t1u}$") or the second threshold angle $\theta_{t1d}$ 204 ("$\theta_A > \theta_{t1d}$") for a period of time greater than a predetermined period of time, then the surgical console 30 determines that the user is disengaged. Although described as being compared to two threshold angles, it is appreciated that any number of threshold angles may be utilized to determine if a user is engaged or disengaged. Additionally, while illustrated in FIGS. 7B and 7C as upward and downward movement of a user's head, it is appreciated that threshold angles may also be associated with side-to-side movement of a user's head for a determination of user disengagement.

Figure 8:
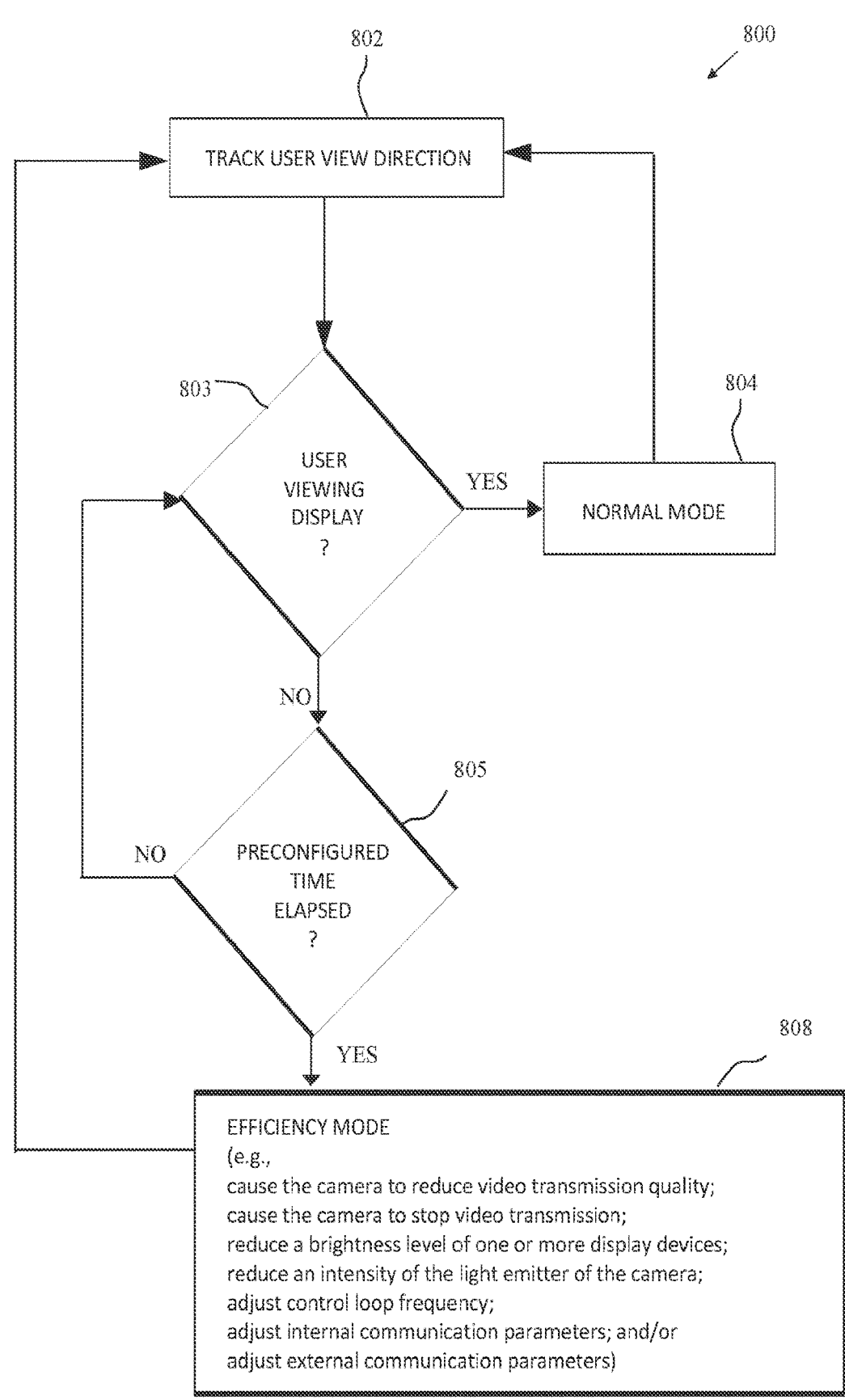
FIG. 8 is a flowchart illustrating an exemplary method for controlling an operational mode of the surgical robotic system of FIG. 1 according to an embodiment of the present disclosure.

FIG. 8 illustrates a method for switching between operating in a normal mode and operating in an efficiency mode in accordance with aspects of the disclosure, and is described as method 800. Method 800 is carried out by any component of surgical robotic system 10, including any of control tower 20, surgical console 30, robotic arm 40, and/or tracking device 320.

Method 800 begins in step 802 and step 803 where a user's view direction is tracked and a determination as to whether the user is viewing a display device (e.g., first display 32) is made, respectively. The user's view direction is tracked and the determination as to whether the user is viewing the display device, may be carried out, for example, in accordance with the description above with respect to FIGS. 7A-C and the determinations of whether a user is engaged or disengaged.

If, in step 803, a determination is made that the user is viewing the display (e.g., first display 32), then all of the components of the robotic surgical system 10 operate in a normal mode of operation. The normal mode of operation may include transmitting the video feed from one or more cameras (e.g., camera 51) at full resolution to one or more display devices (e.g., first display 32, second display 23, etc.), displaying the transmitted video feed on one or more display devices (e.g., first display 32, second display 23, etc.) at full resolution, at full brightness levels, and/or illuminating a light emitter of the camera 51 at full illumination.

If, however, in step 803, a determination is made that the user is not viewing the display (e.g., first display 32), then method 800 proceeds to step 805 where a determination is made as to whether a predetermined amount of time has elapsed since it was determined that the user is not viewing the display. If in step 805, the predetermined amount of time has not elapsed (e.g., the user began viewing the display again within 5 seconds, for example), then method 800 reverts back to step 803 and it can be assumed that although the user turned away from the display, the amount of time in which the user looked away does not justify an assumption that the user is disengaged. Alternatively, if in step 805, a determination is made that a predetermined amount of time has elapsed, then it is assumed that the user is disengaged and method 800 proceeds to step 808.

In step 808, one or more components of the robotic surgical system 10 begin operating in an efficiency mode, which utilizes less bandwidth, consumes less power, and/or generates less heat than when the components of the robotic surgical system 10 are operating in the normal mode. Step 808 may include: 1) reducing the quality of the video transmission from the camera 51 to both of the surgical console 30 and the control tower 20; 2) stopping the video transmission from the camera 51 to the surgical console 30 and the control tower 20; 3) reducing the quality of the video transmission from the camera 51 to the surgical console 30, while maintaining the quality of the video transmission from the camera 51 to the control tower 20; 4) reducing the brightness, turning off, or switching to standby, at least one of the display devices (e.g., first display 32, second display 23, etc.); and/or 5) reducing the intensity of a light emitter of the camera 51 or of another light emitter within the surgical setting. Step 808 may additionally, or alternatively, include one or more of: 1) adjusting a control loop frequency (e.g., reducing a control loop frequency to reduce power consumption and free up bandwidth); 2) adjusting one or more wireless communication parameters (e.g., means of communication or wireless bandwidth consumption) internally between any of the components of the system 10; and/or 3) adjusting one or more wireless communication parameters (e.g., means of communication or wireless bandwidth consumption) externally between any of the components of the system 10 and one or more external components.

When operating in the efficiency mode, reducing the quality of the transmission of the video feed from the camera 51 to any of the display devices of the robotic surgical system 10 reduces the overall bandwidth consumption, thereby increasing the operability and communication speed and reliability between the components of the robotic surgical system 10, and thereby enabling tele-surgical applications of the robotic surgical system 10 with relatively lower network speeds. In an aspect, the reduction in the quality of the video transmission of the video feed from the camera 51 is accomplished by reducing the baud rate, which serves the dual purpose of freeing bandwidth and reducing power consumption and heat generation of components of the robotic surgical system 10. Additionally, when operating in efficiency mode, stopping the display of video, or reducing the brightness or quality of the video displayed on any of the display devices of the robotic surgical system 10 reduces the overall power consumption and heat generation of the components of the robotic surgical system 10. Likewise, when operating in efficiency mode, reducing the intensity of a light emitter on the camera 51 reduces power consumption by the camera 51 and components of the surgical robotic system 10 and reduces the heat generation within the surgical site.

Upon switching to, or remaining to operate in, either of the normal mode or the efficiency mode, method 800 proceeds to step 802. That is, surgical console 30 constantly tracks the user's view direction during operation to repeatedly determine the user's engagement for a determination as to whether the components of the robotic surgical system 10 should be operating in the normal mode, for example to increase performance, or the efficiency mode, for example to increase bandwidth, reduce power consumption, and reduce heat generation.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A robotic surgical system, comprising:
   a robotic arm including a camera coupled thereto, the camera including a light emitter and configured to transmit video; and
   a surgical console including:
   a handle communicatively coupled to at least one of the robotic arm or the camera;
   a display device configured to display video transmitted from the camera;
   a tracking device including an image capture device configured to capture an image of a user position reference point; and
   a computer configured to:
   compute, based on the captured image, a position of the user position reference point relative to the display device;
   determine whether a user is engaged with or disengaged from the surgical console based on the computed position; and
   in response to a determination that the user is disengaged from the surgical console for a predetermined amount of time, perform at least one of the following:
   cause the camera to reduce video transmission quality by reducing a baud rate of the camera or cause the camera to stop video transmission;
   reduce a brightness level of the display device or reduce an intensity of the light emitter of the camera; or
   adjust internal communication parameters between components of the robotic surgical system.

2. The robotic surgical system of claim 1, wherein, in response to a determination that the user is disengaged from the surgical console for a predetermined amount of time, the computer is configured to:
   cause the camera to stop video transmission; and
   reduce the brightness level of the display device.

3. The robotic surgical system of claim 1, wherein, in response to a determination that the user is disengaged from the surgical console for a predetermined amount of time, the computer is configured to:
   cause the camera to reduce video transmission quality or stop video transmission; and
   reduce the intensity of the light emitter.

4. The robotic surgical system of claim 1, further comprising a control tower including a second display device configured to display video transmitted by the camera.

5. The robotic surgical system of claim 4, wherein, in response to a determination that the user is disengaged from the surgical console for a predetermined amount of time, the computer is configured to:

cause the camera to reduce video transmission quality to the second display device of the control tower; and cause the camera to maintain video transmission quality to the display device of the surgical console.

6. The robotic surgical system of claim 4, wherein, in response to a determination that the user is disengaged from the surgical console for a predetermined amount of time, the computer is configured to:

cause the camera to reduce video transmission quality to the display device of the surgical console; and cause the camera to reduce video transmission quality to the second display device of the control tower.

7. The robotic surgical system of claim 4, wherein, in response to a determination that the user is disengaged from the surgical console for a predetermined amount of time, the computer is configured to:

cause the camera to stop video transmission to the display device of the surgical console; and cause the camera to stop video transmission to the second display device of the control tower.

8. A robotic surgical system, comprising:

a camera configured to transmit video; and a surgical console including:

a handle communicatively coupled to a surgical instrument;

a display device configured to display video transmitted from the camera;

a tracking device configured to track a position of a user operating the surgical console; and a computer configured to:

determine whether a user is engaged with or disengaged from the display device of the surgical console based on the tracked position of the user operating the surgical console; and in response to a determination that the user is disengaged from the surgical console for a predetermined amount of time, cause the camera to stop video transmission; and reduce a brightness level of the display device.

9. The robotic surgical system of claim 8, wherein, in response to a determination that the user is disengaged from the surgical console for a predetermined amount of time, the computer is configured to cause the camera to reduce video transmission quality by reducing a baud rate of the camera.

10. The robotic surgical system of claim 8, wherein the camera includes a light emitter and, in response to a determination that the user is disengaged from the surgical console for a predetermined amount of time, the computer is configured to cause the camera to:

reduce video transmission quality or stop video transmission; and reduce an intensity of the light emitter.

11. The robotic surgical system of claim 8, further comprising a control tower including a second display device configured to display video transmitted by the camera.

12. The robotic surgical system of claim 11, wherein, in response to a determination that the user is disengaged from the surgical console for a predetermined amount of time, the computer is configured to:

cause the camera to reduce video transmission quality to the second display device of the control tower; and cause the camera to maintain video transmission quality to the display device of the surgical console.

13. The robotic surgical system of claim 11, wherein, in response to a determination that the user is disengaged from the surgical console for a predetermined amount of time, the computer is configured to:

cause the camera to reduce video transmission quality to the display device of the surgical console; and cause the camera to reduce video transmission quality to the second display device of the control tower.

14. The robotic surgical system of claim 11, wherein, in response to a determination that the user is disengaged from the surgical console for a predetermined amount of time, the computer is configured to cause the camera to stop video transmission to the display device of the surgical console and the second display device of the control tower.

15. A robotic surgical system, comprising:

a robotic arm including a camera coupled thereto, the camera including a light emitter and configured to transmit video;

a control tower including a first display device configured to display video transmitted from the camera; and a surgical console including:

a handle communicatively coupled to at least one of the robotic arm or the camera;

a second display device configured to display video transmitted from the camera;

a tracking device including an image capture device configured to capture an image of a user position reference point; and a computer configured to:

determine whether a user is engaged with or disengaged from the second display device of the surgical console based on a tracked position of the user operating the surgical console; and in response to a determination that the user is disengaged from the surgical console for a predetermined amount of time, perform at least one of the following:

reduce an intensity of the light emitter and cause the camera to reduce video transmission quality or cause the camera to stop video transmission;

reduce a brightness level of the first display device or the second display device; or adjust internal communication parameters between components of the robotic surgical system.

16. The robotic surgical system of claim 15, wherein, in response to a determination that the user is disengaged from the surgical console for a predetermined amount of time, the computer is configured to cause the camera to reduce video transmission quality by reducing a baud rate of the camera.

17. The robotic surgical system of claim 15, wherein, in response to a determination that the user is disengaged from the surgical console for a predetermined amount of time, the computer is configured to cause the camera to:

stop video transmission; and reduce the brightness level of the second display device and maintain the brightness level of the first display device.

\* \* \* \* \*